(12) United States Patent
Whipple

(10) Patent No.: US 11,806,036 B2
(45) Date of Patent: Nov. 7, 2023

(54) POWERED TISSUE RESECTING DEVICE

(71) Applicant: Covidien LP, Mansfield, MA (US)

(72) Inventor: Dale E. Whipple, Nashua, NH (US)

(73) Assignee: Covidien LP, Mansfield, MA (US)

( * ) Notice: Subject to any disclaimer, the term of this patent is extended or adjusted under 35 U.S.C. 154(b) by 341 days.

(21) Appl. No.: 17/124,658

(22) Filed: Dec. 17, 2020

(65) Prior Publication Data

US 2021/0100577 A1    Apr. 8, 2021

Related U.S. Application Data

(63) Continuation of application No. 15/895,407, filed on Feb. 13, 2018, now Pat. No. 10,869,684.

(51) Int. Cl.
*A61B 17/32* (2006.01)
*A61B 17/3205* (2006.01)
(Continued)

(52) U.S. Cl.
CPC .... *A61B 17/32002* (2013.01); *A61B 17/3205* (2013.01); *A61B 17/42* (2013.01);
(Continued)

(58) Field of Classification Search
CPC .......... A61B 17/32002; A61B 17/3205; A61B 17/42; A61B 2017/320028;
(Continued)

(56) References Cited

U.S. PATENT DOCUMENTS

| 1,585,934 A | 5/1926 | Muir |
| 1,666,332 A | 4/1928 | Hirsch |

(Continued)

FOREIGN PATENT DOCUMENTS

| CN | 105559892 A | 5/2016 |
| CN | 106456205 A | 2/2017 |

(Continued)

OTHER PUBLICATIONS

Chinese Office Action issued in corresponding Chinese Application No. 201910088354.9 dated Nov. 3, 2021.
(Continued)

*Primary Examiner* — Alexander J Orkin
(74) *Attorney, Agent, or Firm* — Carter, DeLuca & Farrell LLP

(57) ABSTRACT

A tissue resecting device includes an end effector assembly including a proximal hub housing and a cutting member extending distally from the proximal hub housing, and a handpiece assembly. The handpiece assembly includes a handle housing, a drive casing extending distally from the handle housing, a drive rotor extending through and distally from the drive casing, and a seal ring disposed about the drive rotor. In an at-rest position, the seal ring is sealingly engaged between the drive casing and the drive rotor to inhibit fluid ingress into the annular space. Upon engagement of the end effector assembly with the handpiece assembly, a portion of the proximal hub housing is configured to urge the seal ring from the at-rest position to a displaced position wherein the seal ring is displaced from the drive rotor to reduce friction therebetween upon rotation of the drive rotor relative to the drive casing.

10 Claims, 5 Drawing Sheets

(51) Int. Cl.
*A61B 17/42* (2006.01)
*A61B 17/00* (2006.01)
*A61B 17/29* (2006.01)
*A61B 90/00* (2016.01)

(52) U.S. Cl.
CPC ............ *A61B 2017/00477* (2013.01); *A61B 2017/2948* (2013.01); *A61B 2017/320028* (2013.01); *A61B 2017/320032* (2013.01); *A61B 2090/0813* (2016.02); *A61B 2217/005* (2013.01); *A61B 2217/007* (2013.01)

(58) Field of Classification Search
CPC ......... A61B 2017/320032; A61B 2017/00477; A61B 2090/0813; A61B 2217/005; A61B 2217/007
See application file for complete search history.

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,178 A | 10/1996 | Henley |
| 5,569,254 A | 10/1996 | Carlson et al. |
| 5,569,284 A | 10/1996 | Young et al. |
| 5,575,756 A | 11/1996 | Karasawa et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |

(56) References Cited

U.S. PATENT DOCUMENTS

| | | |
|---|---|---|
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,022,363 A | 2/2000 | Walker et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,171,316 B1 | 1/2001 | Kovac et al. |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,293,957 B1 | 9/2001 | Peters et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,663,641 B1 | 12/2003 | Kovac et al. |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,062,214 B2 | 11/2011 | Shener et al. |
| 8,419,626 B2 | 4/2013 | Shener-Irmakoglu et al. |
| 8,574,253 B2 | 11/2013 | Gruber et al. |
| 8,663,264 B2 | 3/2014 | Cesarini et al. |
| 8,678,999 B2 | 3/2014 | Isaacson |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,050,133 B1 * | 6/2015 | Boone, III ............ A61B 17/545 |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,125,550 B2 | 9/2015 | Shener-Irmakoglu et al. |
| 9,155,454 B2 | 10/2015 | Sahney et al. |
| 10,869,684 B2 | 12/2020 | Whipple |
| 2001/0039963 A1 | 11/2001 | Spear et al. |
| 2001/0047183 A1 | 11/2001 | Privitera et al. |
| 2002/0058859 A1 | 5/2002 | Brommersma |
| 2002/0165427 A1 | 11/2002 | Yachia et al. |
| 2003/0050603 A1 | 3/2003 | Todd |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2004/0010258 A1 | 1/2004 | Carusillo et al. |
| 2004/0204671 A1 | 10/2004 | Stubbs et al. |
| 2004/0220602 A1 | 11/2004 | Deng et al. |
| 2005/0043690 A1 | 2/2005 | Todd |
| 2005/0085692 A1 | 4/2005 | Kiehn et al. |
| 2005/0096649 A1 * | 5/2005 | Adams ................ A61B 18/149 606/171 |
| 2006/0036132 A1 | 2/2006 | Renner et al. |
| 2006/0047185 A1 | 3/2006 | Shener |
| 2006/0161191 A1 | 7/2006 | Bucina |
| 2006/0241586 A1 | 10/2006 | Wilk |
| 2007/0021752 A1 | 1/2007 | Rogers |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0188848 A1 | 8/2008 | Deutmeyer |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0100112 A1 | 4/2010 | Kauker |
| 2010/0125287 A1 | 5/2010 | Cole et al. |
| 2010/0152647 A1 | 6/2010 | Shener et al. |
| 2011/0098688 A1 * | 4/2011 | Gigon ................ A61B 17/1688 606/1 |
| 2011/0166419 A1 | 7/2011 | Reif et al. |
| 2012/0078038 A1 | 3/2012 | Sahney et al. |
| 2012/0209289 A1 | 8/2012 | Duque et al. |

(56) References Cited

U.S. PATENT DOCUMENTS

| | | | |
|---|---|---|---|
| 2012/0253227 A1 | 10/2012 | Shener-Irmakoglu et al. | |
| 2013/0131452 A1 | 5/2013 | Kuroda et al. | |
| 2014/0031834 A1 | 1/2014 | Germain et al. | |
| 2016/0184046 A1* | 6/2016 | Blain .................. | A61B 17/1659 600/249 |
| 2017/0020545 A1 | 1/2017 | Loreth | |
| 2017/0360466 A1* | 12/2017 | Brown ............. | A61B 17/32002 |

FOREIGN PATENT DOCUMENTS

| | | |
|---|---|---|
| DE | 102010050352 A1 | 5/2012 |
| EP | 1753350 B1 | 8/2014 |
| WO | 2015023965 A1 | 2/2015 |

OTHER PUBLICATIONS

Partial European Search Report issued in corresponding European Application No. 19156616.5 dated Jun. 14, 2019, 11 pages.
Extended European Search Report issued in European Application No. 19156616.5 dated Sep. 18, 2019, 9 pages.

\* cited by examiner

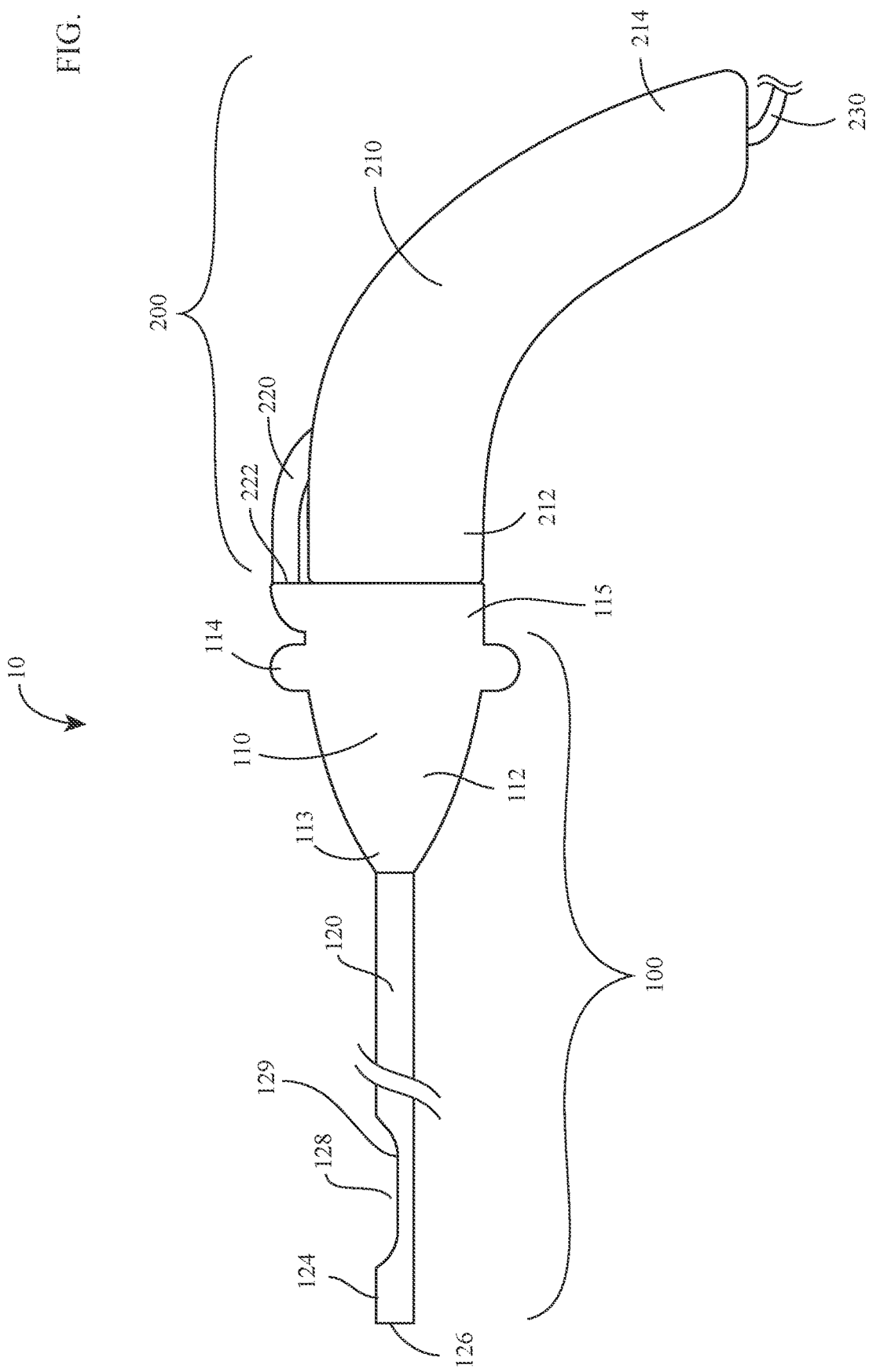

POWERED TISSUE RESECTING DEVICE

CROSS REFERENCE TO RELATED APPLICATION

The present application is a Continuation Application of U.S. patent application Ser. No. 15/895,407, filed on Feb. 13, 2018, the entire content of which is incorporated by reference herein.

BACKGROUND

1. Technical Field

The present disclosure relates generally to the field of tissue resection. In particular, the present disclosure relates to a powered tissue resecting device.

2. Background of Related Art

Tissue resection may be performed endoscopically within an organ, such as a uterus, by inserting an endoscope (or hysteroscope) into the uterus and passing a tissue resection device through the endoscope (or hysteroscope) and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

SUMMARY

As used herein, the term "distal" refers to the portion that is described which is further from a user, while the term "proximal" refers to the portion that is described which is closer to a user. Further, to the extent consistent, any or all of the aspects described herein may be used in conjunction with any or all of the other aspects described herein.

Provided in accordance with aspects of the present disclosure is a tissue resecting device including an end effector assembly and a handpiece assembly. The end effector assembly includes a proximal hub housing and a cutting member extending distally from the proximal hub housing. The handpiece assembly includes a handle housing, a drive casing extending distally from the handle housing, a drive rotor extending through and distally from the drive casing, and a seal ring disposed about the drive rotor. In an at-rest position, the seal ring is sealingly engaged between the drive casing and the drive rotor to inhibit fluid ingress into the annular space. The end effector assembly is releasably engagable with the handpiece assembly. Upon engagement of the end effector assembly with the handpiece assembly, a portion of the proximal hub housing is configured to urge the seal ring from the at-rest position to a displaced position wherein the seal ring is displaced from the drive rotor to reduce friction therebetween upon rotation of the drive rotor relative to the drive casing.

In an aspect of the present disclosure, the end effector assembly further includes an inner core disposed within the proximal hub housing. In such aspects, the cutting member is coupled to the inner core and the inner core is configured to couple to the drive rotor upon engagement of the end effector assembly with the handpiece assembly such that rotation of the drive rotor drives the cutting member. The inner core, in aspects, is configured such that rotation of the drive rotor drives rotation and reciprocation of the cutting member.

In another aspect of the present disclosure, the end effector assembly further includes a fixed outer shaft extending distally from the proximal hub housing and disposed about the cutting member.

In yet another aspect of the present disclosure, the proximal hub housing defines bayonet threading and the drive casing defines bayonet threading configured to engage the bayonet threading of the proximal hub housing to engage the end effector assembly with the handpiece assembly.

In still another aspect of the present disclosure, the handpiece assembly further includes a motor disposed within the handle housing and configured to drive rotation of the drive rotor.

Another tissue resecting device provided in accordance with aspects of the present disclosure includes a handpiece assembly including a drive rotor and an end effector assembly configured to engage the handpiece assembly. The end effector assembly defines a longitudinal axis and includes a proximal hub housing defining a fluid channel including an input disposed in a radially-inward facing direction relative to the longitudinal axis and an output, an inner core operably disposed within the proximal hub housing and configured to couple to the drive rotor such that rotation of the drive rotor effects rotation and reciprocation of the inner core relative to the proximal hub housing, a cutting member extending distally from the proximal hub housing and coupled to the inner core such that rotation and reciprocation of the inner core rotation relative to the proximal hub housing effects rotation and reciprocation of the cutting member relative to the proximal hub housing, and a valve disposed within the proximal hub housing. The valve is transitionable between an open position, permitting fluid flow from the cutting member into the input of the fluid channel, and a closed position, inhibiting fluid flow from the cutting member into the input of the fluid channel. The valve is disposed in the open position during a first portion of the reciprocation motion of the inner core and in the closed position during a second, different portion of the reciprocation motion of the inner core. Transitioning of the valve from the closed position to the open position establishes a surge of centrifugal force to urge fluid from the cutting member into the input of the fluid channel.

In an aspect of the present disclosure, the handpiece assembly further includes a fluid conduit configured to couple to the output of the fluid channel to receive fluid therefrom. In such aspects, the fluid conduit may be adapted to connect to a suction source to apply suction through the fluid conduit, the fluid channel, and the cutting member when the valve is disposed in the open position. Further, the surge of centrifugal force may be greater than a steady-state suction force applied from the suction source.

In another aspect of the present disclosure, the inner core is configured to reciprocate through the proximal hub housing between a proximal position and a distal position. In such aspects, the valve is disposed in the open position when the inner core is disposed towards the proximal position, and the valve is disposed in the closed position when the inner core is disposed towards the distal position.

In yet another aspect of the present disclosure, the end effector assembly further includes a fixed outer shaft extending distally from the proximal hub housing and disposed about the cutting member.

In still another aspect of the present disclosure, the valve is defined by the inner core and an inner housing of the proximal hub housing.

Another tissue resecting device provided in accordance with aspects of the present disclosure includes an end effector assembly including a proximal hub housing and a cutting member extending distally from the proximal hub housing. The proximal hub housing defines a fluid channel therethrough configured to enable withdrawal of fluid from the cutting member. A portion of the proximal hub housing adjacent the fluid channel is formed from a heat sink material. The tissue resecting device further includes a handpiece assembly including a handle housing, a drive rotor extending distally from the handle housing and configured to couple the cutting member to drive the cutting member, a motor disposed within the handle housing and configured to drive the drive rotor to thereby drive the cutting member, and a drive casing extending distally from the handle housing and disposed about a portion of the drive rotor. A portion of the drive casing is formed from a heat sink material. The proximal hub housing is configured to engage the drive casing to releasably engage the end effector assembly with the handpiece assembly. With the end effector assembly engaged with the handpiece assembly, the portion of the proximal hub housing and the portion of the drive casing are disposed in direct thermal communication with one another to form a heat sink for conducting heat from the motor to fluid flowing through the fluid channel, thereby helping to cool the motor.

In an aspect of the present disclosure, the proximal hub housing defines bayonet threading and the drive casing defines bayonet threading configured to engage the bayonet threading of the proximal hub housing to engage the end effector assembly with the handpiece assembly and bring the portion of the proximal hub housing and the portion of the drive casing into direct thermal communication with one another to form the heat sink.

In another aspect of the present disclosure, the heat sink material of the portion of the proximal hub housing and/or the heat sink material of the portion of the drive casing is a thermally-conductive metal.

In still another aspect of the present disclosure, the motor is configured to drive rotation of the drive rotor.

In yet another aspect of the present disclosure, the end effector assembly further includes an inner core configured to couple the drive rotor with the cutting member. The inner core is configured such that rotation of the drive rotor drives rotation and reciprocation of the cutting member.

In still yet another aspect of the present disclosure, the end effector assembly further includes a fixed outer shaft extending distally from the proximal hub housing and disposed about the cutting member.

In another aspect of the present disclosure, the handpiece assembly further includes a fluid conduit configured to couple to an output of the fluid channel to receive fluid therefrom. The fluid conduit is adapted to connect to a suction source to apply suction through the fluid conduit, the fluid channel, and the cutting member to withdraw fluid therefrom.

BRIEF DESCRIPTION OF THE DRAWINGS

Various aspects and features of the present disclosure are described hereinbelow with reference to the drawings wherein like numerals designate identical or corresponding elements in each of the several views and:

FIG. 1 is a side view of a tissue resecting device provide in accordance with aspects of the present disclosure;

DETAILED DESCRIPTION

Referring generally to FIG. 1, a tissue resecting device 10 provided in accordance with the present disclosure and configured to resect tissue includes an end effector assembly 100 and a handpiece assembly 200. Tissue resecting device 10 is adapted to connect to a control unit (not shown) to provide power and control functionality to tissue resecting device 10, although tissue resecting device 10 may alternatively or additionally include controls associated with handpiece assembly 200 and/or a power source, e.g., battery, disposed within handpiece assembly 200. Tissue resecting device 10 is further adapted to connect to a fluid management system (not shown) for removing fluid, tissue, and debris from a surgical site via tissue resecting device 10. The control unit and fluid management system may be integral with one another, coupled to one another, or separate from one another.

With continued reference to FIG. 1, tissue resecting device 10 may be configured as a single-use device that is discarded after use or sent to a manufacturer for reprocessing, a reusable device capable of being cleaned and/or sterilized for repeated use by the end-user, or a partially-single-use, partially-reusable device. With respect to partially-single-use, partially-reusable configurations, handpiece assembly 200 may be configured as a cleanable/sterilizable, reusable component, while end effector assembly 100 is configured as a single-use, disposable/reprocessable component. In either of the above configurations, end effector assembly 100 is configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for use of different end effector assemblies, e.g., end effector assembly 100 (FIGS. 1 and 2A) or end effector assembly 1100 (FIG. 2B), with handpiece assembly 200.

Figure 2A:
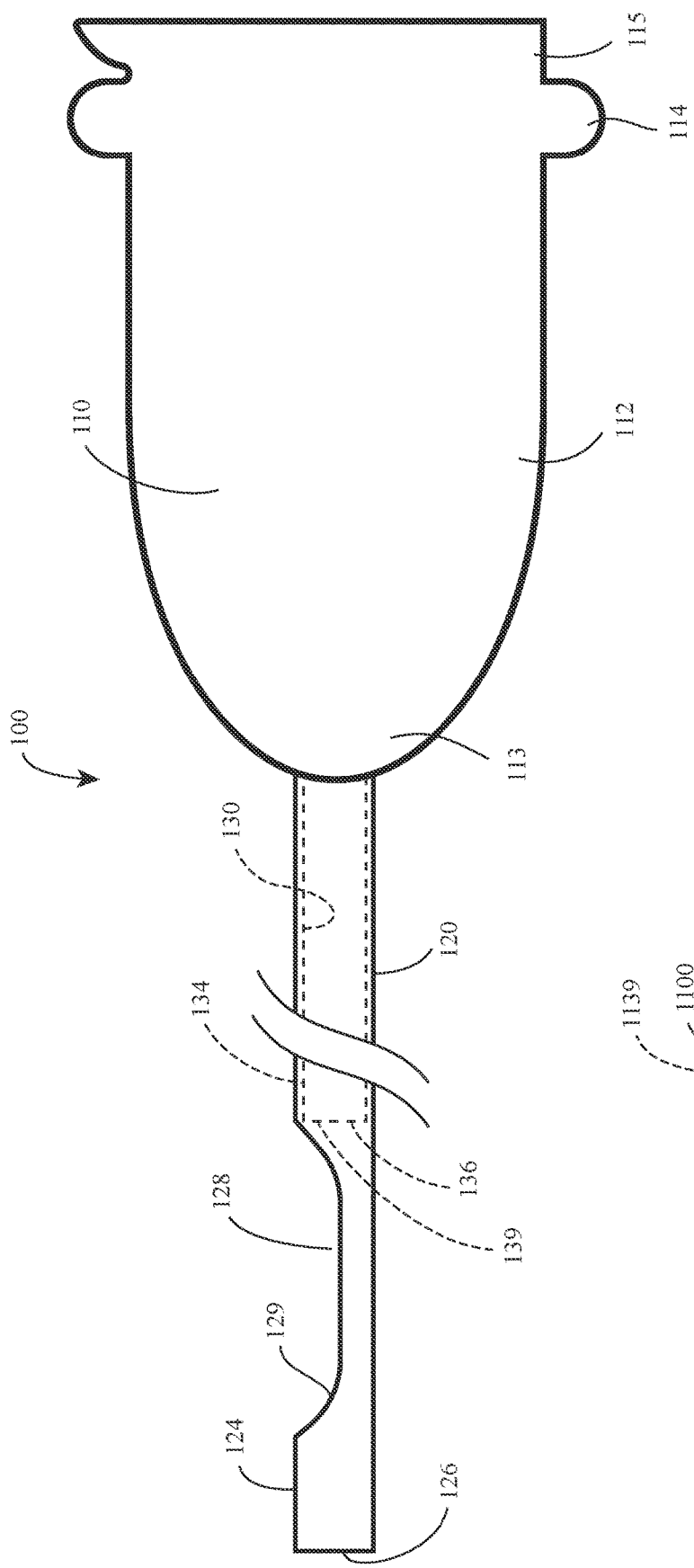
FIG. 2A is a side view of an end effector assembly of the tissue resecting device of FIG. 1.
Figure 3:
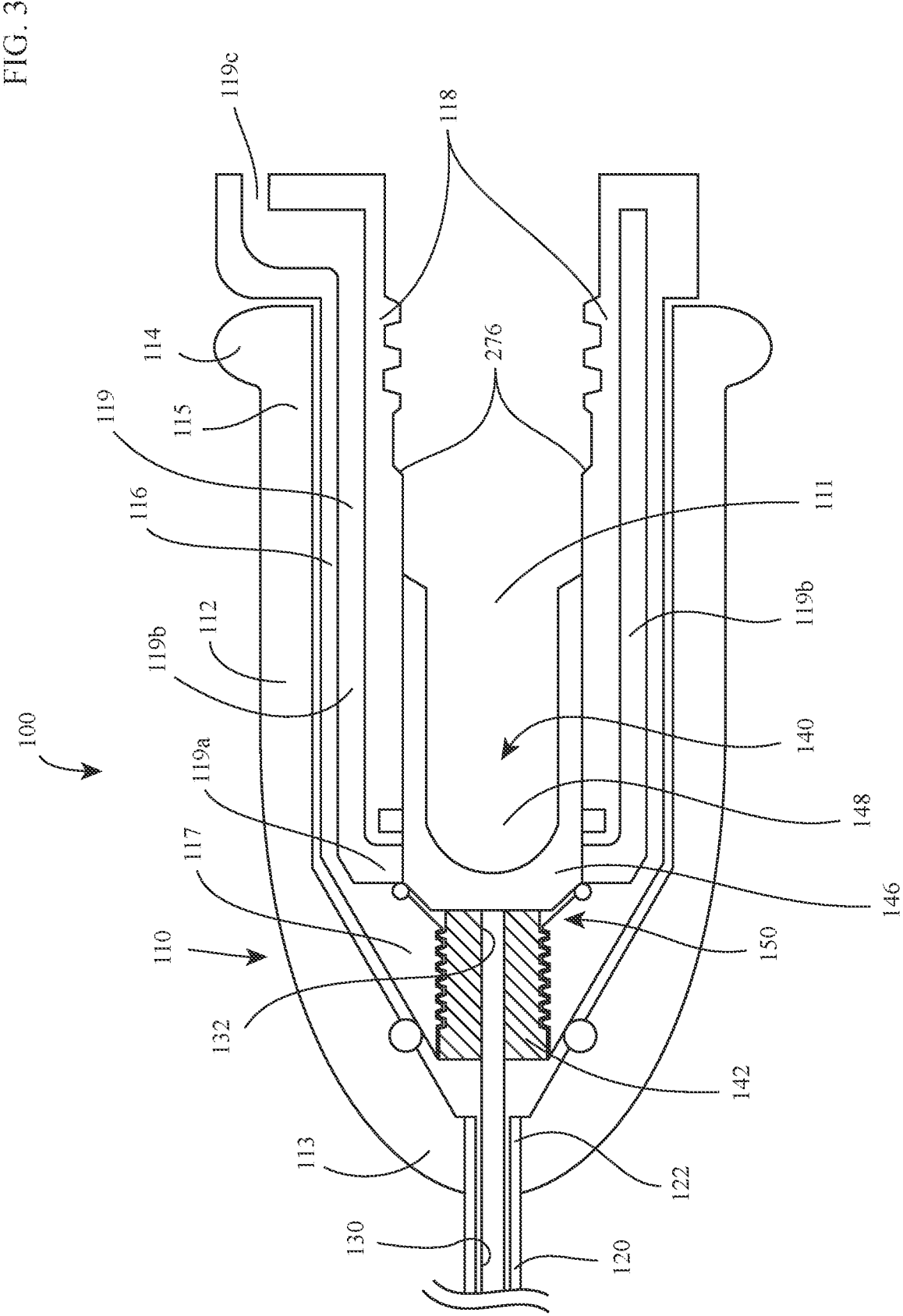
FIG. 3 is a longitudinal, cross-sectional view of a proximal portion of the end effector assembly of FIG. 2A.

Referring to FIGS. 2A and 3, end effector assembly 100 includes a proximal hub housing 110, an elongated outer shaft 120 fixedly engaged with and extending distally from proximal hub housing 110, an inner cutting shaft 130 movable disposed within elongated outer shaft 120, and an inner drive core 140 operably disposed within proximal hub housing 110 and coupled to inner cutting shaft 130 such that rotational input imparted to inner drive core 140, e.g., via handpiece assembly 200, as detailed below, drives reciprocation and rotation of inner cutting shaft 130 within and relative to elongated outer shaft 120.

Proximal hub housing 110 of end effector assembly 100 includes an outer housing 112 and an inner housing 116 sealingly engaged within outer housing 112. Outer housing 112 receives and fixedly engages a proximal end portion 122 of elongated outer shaft 120 therein at a distal nose 113 of outer housing 112. Outer housing 112 further includes an annular protrusion 114 defined at proximal base 115 of outer housing 112 to facilitate grasping and manipulating proximal hub housing 110. Inner housing 116 includes a threaded distal nose 117, proximal bayonet threading 118 disposed within and facing radially-inwardly into an interior cavity 111 of proximal hub housing 110, and an annular channel 119 disposed about interior cavity 111 and defining a radially-inwardly-facing open distal end 119a, a ring-shaped body 119b, and a proximal exit port 119c. Inner housing 116, or at least a portion thereof, is formed from a heat sink material, e.g., a thermally-conductive material such as a metal, to serve as a heat sink for motor 260 of handpiece assembly 200 (FIG. 4), as detailed below.

Elongated outer shaft 120 of end effector assembly 100, as noted above, includes a proximal end portion 122 fixedly engaged with outer housing 112 of proximal hub housing 110. Elongated outer shaft 120 further includes a distal end portion 124 defining a closed distal end 126 and a window 128 proximally-spaced from closed distal end 126. Window 128 provides access to the interior of elongated outer shaft 120 and may be surrounded by a cutting edge 129 about the outer perimeter of window 128 so as to facilitate cutting of tissue passing through window 128 and into elongated outer shaft 120.

Inner cutting shaft 130 defines a proximal end portion 132 and a distal end portion 134 defining an open distal end 136. Inner cutting shaft 130 defines an annular cutting edge 138 surrounding open distal end 136 so as to facilitate cutting of tissue passing into inner cutting shaft 130 via open distal end 136. Inner cutting shaft 130, as noted above, is rotatable and reciprocatable within and relative to elongated outer shaft 120. More specifically, inner cutting shaft 130 is configured to reciprocate and rotate such that annular cutting edge 138 is exposed within window 128 of elongated outer shaft 120 during at least a portion of the reciprocation motion of inner cutting shaft 130 to enable cutting of tissue therewith. As detailed below, suction is provided to facilitate drawing tissue into window 128 and, thus, cutting and removal of tissue through inner cutting shaft 130.

Figure 2B:
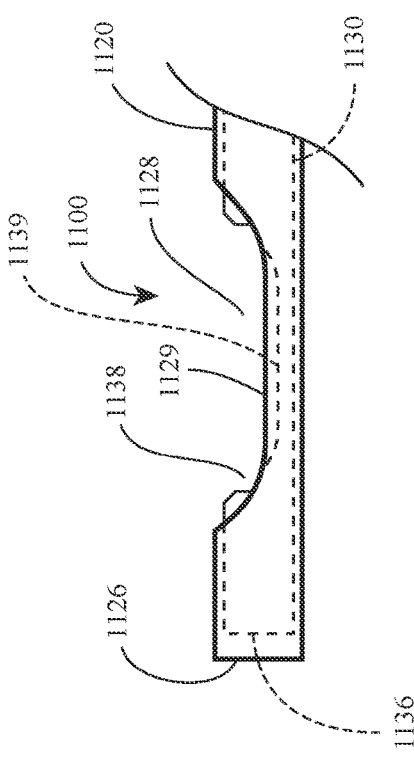
FIG. 2B is a side view of a distal end portion of another end effector assembly configured for use with the tissue resecting device of FIG. 1.

With momentary reference to FIG. 2B, another embodiment of an end effector assembly 1100 configured for use with tissue resecting deice 10 (FIG. 1) is shown. End effector assembly 1100 is similar to and may include any of the features of end effector assembly 100 (FIG. 2A), except that, rather than reciprocation and rotation, inner cutting shaft 1130 of end effector assembly 1100 is longitudinally fixed and rotatable relative to elongated outer shaft 1120. End effector assembly 1100 further differs from end effector assembly 100 (FIG. 2A) in that elongated outer shaft 1120 and inner cutting shaft 1130 both define window 1128, 1138 proximally-spaced from the respective distal end 1126, 1136 thereof. Window 1128 and/or window 1138 may be surrounded by a cutting edge 1129, 1139, respectively, configured to facilitate cutting of tissue passing through windows 1128, 1138 upon relative rotation between windows 1128, 1138, e.g., as a result of rotation of inner cutting shaft 1130 relative to elongated outer shaft 1120. Other suitable end effector assemblies including various different elongated outer shaft and inner cutting shaft configurations are also contemplated.

Referring again to FIGS. 2A and 3, inner drive core 140 of end effector assembly 100 includes a threaded ferrule 142 defining threading on an exterior thereof and a receiver 146 engaged to and extending proximally from threaded ferrule 142. Threaded ferrule 142 is engaged about proximal end portion 132 of inner cutting shaft 130 such that rotation of threaded ferrule 142 effects corresponding rotation of inner cutting shaft 130. Threaded ferrule 142 is disposed within threaded distal nose 117 of inner housing 116 with the respective threads thereof disposed in meshed engagement with one another. As a result of this configuration, rotational input to threaded ferrule 142 effects rotation and reciprocation of threaded ferrule 142 through and relative to proximal hub housing 110 which, in turn, rotates and reciprocates inner cutting shaft 130 relative to elongated outer shaft 120.

Receiver 146 of inner drive core 140, as noted above, is engaged to and extends proximally from threaded ferrule 142. Receiver 146 is slidably and rotatably disposed within interior cavity 111 of proximal hub housing 110 and defines a slot 148 having a non-circular cross-section. Slot 148 is configured to receive a drive rotor 250 of handpiece assembly 200 (see FIGS. 4-5B) in fixed rotational orientation relative thereto such that rotation of drive rotor 250 is imparted to receiver 146 which, in turn, is imparted to threaded ferrule 142 to rotate and reciprocate inner cutting shaft 130 relative to elongated outer shaft 120.

With continued reference to FIGS. 2A and 3, as noted above, annular channel 119 defined within inner housing 116 has a radially-inwardly-facing open distal end 119a, a ring-shaped body 119b, and a proximal exit port 119c. Radially-inwardly-facing open distal end 119a is oriented perpendicularly relative to a longitudinal axis of elongated outer shaft 120 and inner cutting shaft 130 and, thus, perpendicular to the direction of fluid, tissue, and debris flow through inner cutting shaft 130. Further, inner housing 116 and receiver 146 cooperate to define a valve 150 between radially-inwardly-facing open distal end 119a of annular channel 119 and the open proximal end of inner cutting shaft 130. More specifically, as receiver 146 reciprocates through and relative to inner housing 116, receiver 146 is moved from a proximal position, corresponding to an open position of valve 150 (see FIG. 5B), enabling fluid communication between the interior of inner cutting shaft 130 and annular channel 119, and a distal position, corresponding to a closed position of valve 150 (FIG. 5A), wherein receiver 146 abuts threaded distal nose 117 of inner housing 116 in sealing engagement therewith to inhibit fluid communication between the interior of inner cutting shaft 130 and annular channel 119. Thus, during use, when end effector assembly 100 is activated such that inner cutting shaft 130 is rotating and reciprocating, valve 150 is open during a portion of the rotating and reciprocating, and is closed during another portion of the rotating and reciprocating. When valve 150 is open, fluid, tissue and debris suctioned into inner cutting shaft 130 are be evacuated from end effector assembly 100 via annular channel 119, as detailed below.

Figure 4:
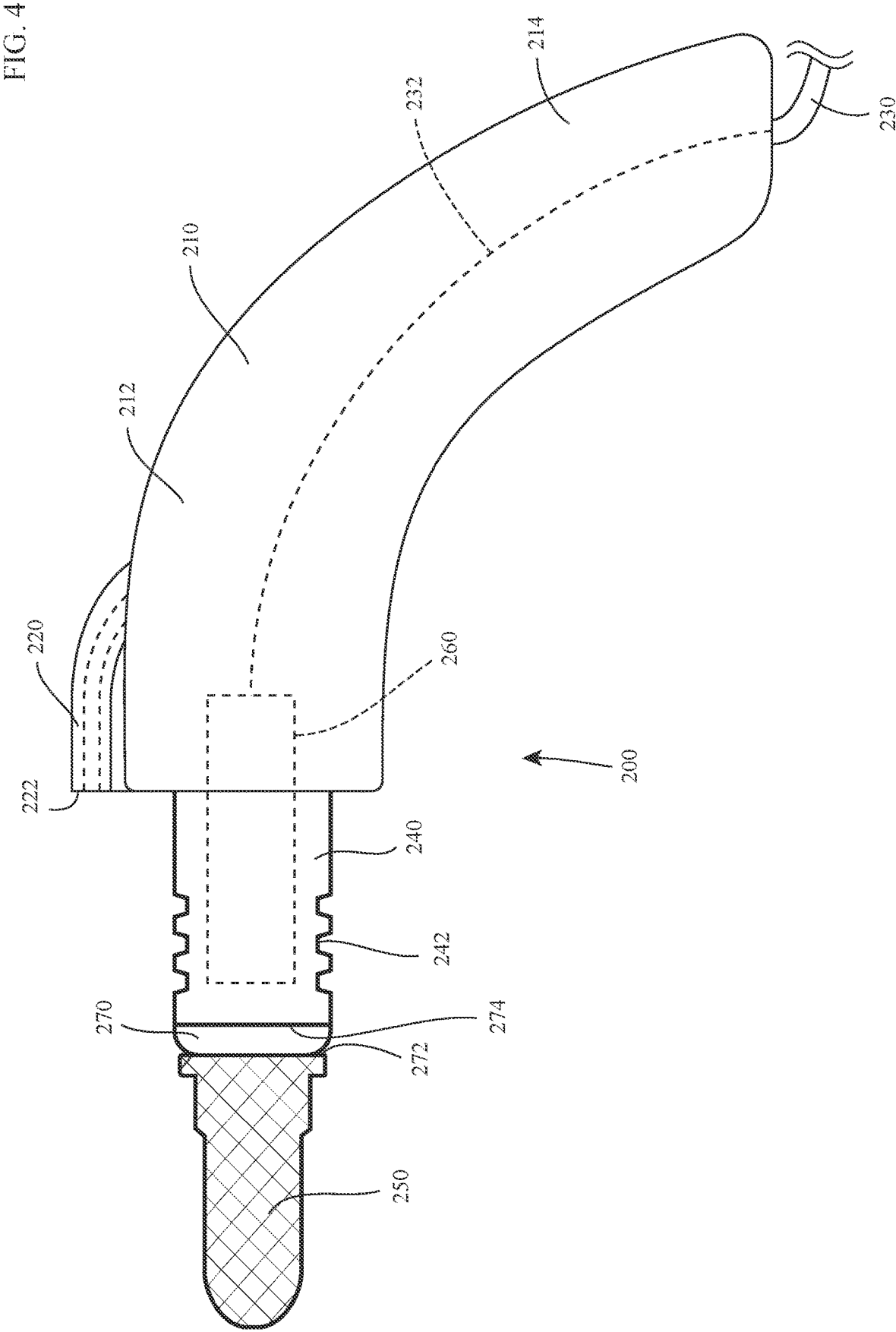
FIG. 4 is a side view of a handpiece assembly of the tissue resecting device of FIG. 1.

Turning now to FIGS. 1, 3, and 4, handpiece assembly 200 generally includes a handle housing 210, a fluid return conduit 220 disposed on handle housing 210, a cable 230 coupled to handle housing 210, a drive casing 240 extending distally from handle housing 210, a drive rotor 250 extending distally from drive casing 240, and a motor 260 disposed within at least a portion of drive casing 240 and/or handle housing 210. Handpiece assembly 200 may further include one or more controls (not shown) disposed on or operably associated with handle housing 210 to facilitate activation of tissue resecting device 10.

Handle housing 210 defines a pistol-grip configuration, although other configurations are also contemplated, and includes a barrel portion 212 and a fixed handle portion 214. Fluid return conduit 220 extends alongside barrel portion 212 of handle housing 210 and may be formed with barrel portion 212 or otherwise engaged thereto. Fluid return conduit 220 defines an open distal end 222 that is configured to abut and operably couple with proximal exit port 119c of end effector assembly 100 (FIGS. 2A and 3) upon engagement of end effector assembly 100 with handpiece assembly 200 so as to define a continuous fluid path from end effector assembly 100, through fluid return conduit 220, to a collection receptacle of the fluid management system (not shown). To this end, fluid return conduit 220 may be coupled at its proximal end to tubing (not shown) or other suitable structure configured to direct fluid from fluid return conduit 220 to the fluid management system.

Cable 230 extends proximally from fixed handle portion 214 of handle housing 210 and is configured to connect to the control unit (not shown) to provide power and control functionality to tissue resecting device 10. Cable 230, more specifically, houses one or more wires 232 that extend into handle housing 210 and connect to the controls thereof and/or motor 260 to power motor 260 and control operation of tissue resecting device 10 in accordance with controls associated with handpiece assembly 200, the control unit, and/or other remote control devices, e.g., a footswitch (not shown).

The drive casing 240, as noted above, extend distally from handle housing 210. Drive casing 240, more specifically, surrounds at least a portion of motor 260, is disposed in thermal communication with motor 260, and is formed from a heat sink material, e.g., a thermally-conductive material such as a metal, to serve as a heat sink for motor 260. Drive casing 240 further defines external bayonet threading 242 therein that is configured to engage proximal bayonet threading 118 of inner housing 116 of end effector assembly 100 to releasably engage end effector assembly 100 with handpiece assembly 200.

Drive rotor 250 extends distally from drive casing 240, as noted above, and defines a non-circular cross-section complementary to that of slot 148 of receiver 146 of end effector assembly 100 such that, upon engagement of end effector assembly 100 with handpiece assembly 200, drive rotor 250 is received within slot 148 of receiver 146 in fixed rotational orientation relative thereto. As such, rotation of drive rotor 250 is imparted to receiver 146 which, in turn, is imparted to threaded ferrule 142 to rotate and reciprocate inner cutting shaft 130 relative to elongated outer shaft 120. An annular gap is defined between drive rotor 250 and drive casing 240 to enable drive rotor 250 to rotate relative to drive casing 240 with minimal friction therebetween.

Referring to FIG. 4, a seal ring 270 formed from an elastomeric material is disposed, in an at-rest position, about drive rotor 250 between a proximally-facing shoulder 272 of drive rotor 250 and a distally-facing surface 274 of drive casing 240 so as to seal the annular gap defined between drive rotor 250 and drive casing 240. Thus, fluids are inhibited from entering the annular gap defined between drive rotor 250 and drive casing 240 such as, for example, during sterilization and/or cleaning of handpiece assembly 200 for reuse.

Figure 5A:
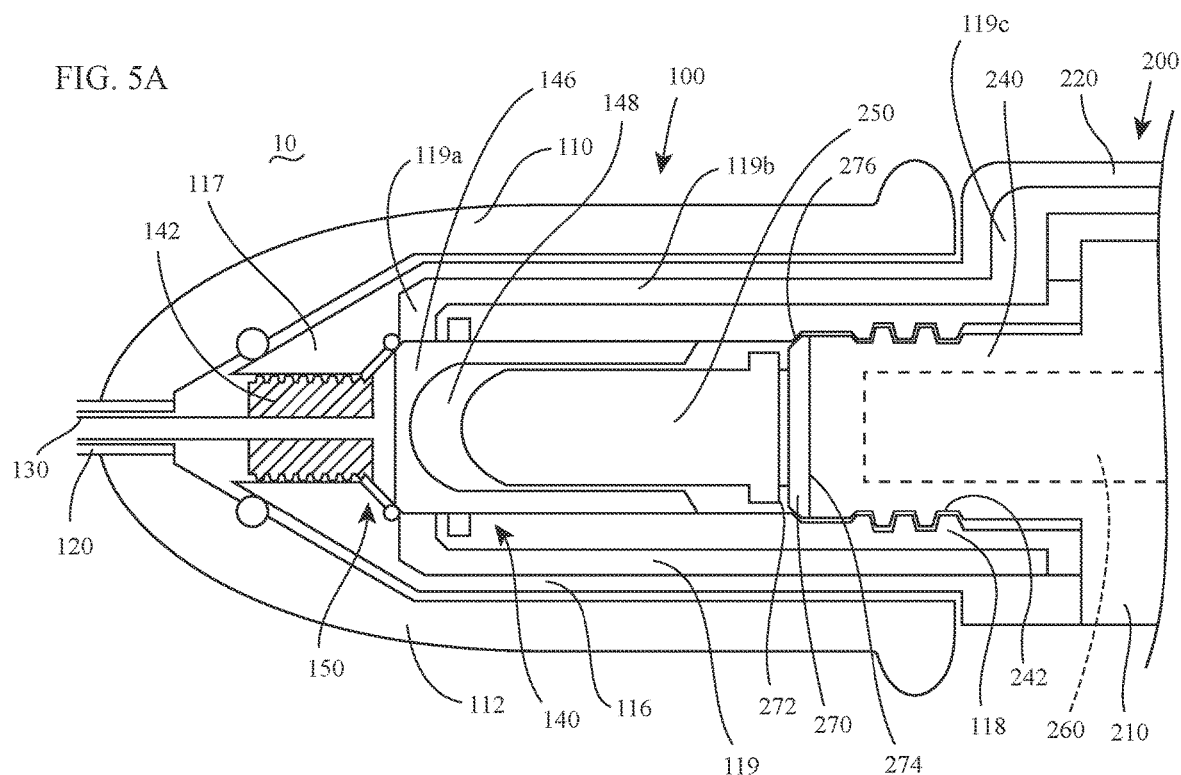
FIG. 5A is a longitudinal, cross-sectional view illustrating the proximal portion of the end effector assembly engaged with a distal portion of the handpiece assembly, wherein internal operating components thereof are in a first position during use.
Figure 5B:
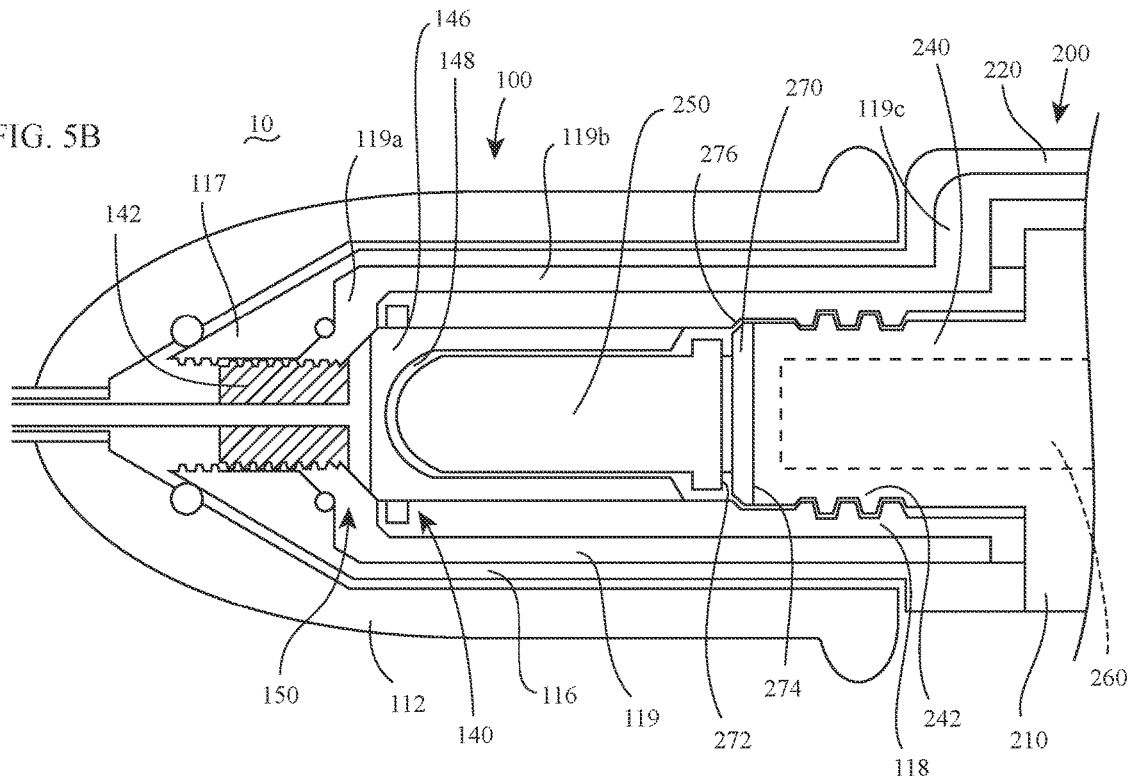
FIG. 5B is a longitudinal, cross-sectional view illustrating the proximal portion of the end effector assembly engaged with the distal portion of the handpiece assembly, wherein the internal operating components thereof are in a second position during use.

Turning to FIGS. 5A-5B, in conjunction with FIGS. 1, 3, and 4, in order to engage end effector assembly 100 with handpiece assembly 200, end effector assembly 100 is approximated and rotated relative to handpiece assembly 200 to engage external bayonet threading 242 of drive casing 240 with proximal bayonet threading 118 of inner housing 116 and such that open distal end 222 of fluid return conduit 220 is operably coupled with proximal exit port 119c of annular channel 119 and drive rotor 250 is received within receiver 146 in fixed rotational engagement therewith. In this engaged condition, fluid, tissue, and debris are permitted to flow (when valve 150 is disposed in the open position) from inner cutting shaft 130 through annular channel 119 and into fluid return conduit 220 for ultimate collection at the fluid management system. Further, in this engaged condition, inner housing 116 and drive casing 240 are thus disposed in contact with one another to together serve as a heat sink conducting heat away from motor 260 to fluid passing through annular channel 119 defined within inner housing 116 during use, thus helping to cool motor 260.

Additionally, upon engagement of end effector assembly 100 with handpiece assembly 200, a ramped surface 276 of inner housing 116 urges seal ring 270 proximally such that seal ring 270 is displaced from proximally-facing shoulder 272 of drive rotor 250 and removed from contact with drive rotor 250. As such, friction between seal ring 270, drive rotor 250, and drive casing 240 during use, e.g., rotation of drive rotor 250 relative to drive casing 240, is substantially reduced if not eliminated. Upon disengagement of end effector assembly 100 from handpiece assembly 200, seal ring 270 is returned under bias to its at-rest position.

Referring generally to FIGS. 1, 2A, and 3-5B, prior to use, tissue resecting device 10 is assembled by engaging end effector assembly 100 with handpiece assembly 200, as detailed above. Further, cable 230 is connected to the control unit and fluid return conduit 220 is connected to the fluid management system. Once this is achieved, tissue resecting device 10 is ready for use. In use, tissue resecting device 10 is positioned within an internal body cavity or organ, e.g., a uterus, such that the distal end portion of end effector assembly 100 is positioned adjacent tissue to be removed. Tissue resecting device 10 may be inserted through an endoscope, e.g., a hysteroscope, or other device, or may be used independently.

Once tissue resecting device 10 is positioned as desired adjacent tissue to be removed, tissue resecting device 10 is activated. Activation of tissue resecting device 10 powers motor 260 which serves to rotationally drive rotor 250. Rotation of drive rotor 250, in turn, provides rotational input to receiver 146 such that threaded ferrule 142 is rotated and reciprocated to thereby rotate and reciprocate inner cutting shaft 130 relative to elongated outer shaft 120. Activation of tissue resecting device 10 also serves to activate suction through fluid return conduit 220, thereby applying suction through inner cutting shaft 130. With such suction applied, tissue is drawn through window 128 of elongated outer shaft 120 and into inner cutting shaft 130, while cutting edges 129, 138 facilitate cutting of tissue as it passes through window 128 and into inner cutting shaft 130. The suction also draws fluid and debris into inner cutting shaft 130. Tissue resecting device 10 is utilized until the desired tissue is removed from the internal body cavity or organ.

The tissue, fluid, and debris suctioned through inner cutting shaft 130 travel proximally through inner cutting shaft 130, eventually reaching valve 150. With valve 150 in the open position (FIG. 5B), the tissue, fluid, and debris are urged radially outwardly, into and through the radially-inwardly-facing open distal end 119a of annular channel 119 and eventually passing through ring-shaped body 119b of annular channel 119, proximal exit port 119c of annular channel 119, and into fluid return conduit 220. When valve 150 is disposed in the closed position (FIG. 5A), the tissue, fluid, and debris do not pass therethrough; however, upon re-opening of valve 150, a centrifugal force surge (created due to the rotation of receiver 146 relative to inner housing 116 and the perpendicular orientation open distal end 119a of annular channel 119 relative to the longitudinal axis of elongated outer shaft 120) above the steady-state suction force urges the tissue, fluid, and debris radially outwardly into open distal end 119a of annular channel 119 such that any collected tissue, fluid, and debris is taken therewith under this force surge, thus clearing any collected tissue, fluid, and debris and inhibiting clogging within proximal hub housing 110 of end effector assembly 100. Further, as noted above, the fluid (and tissue and debris) passing proximally through annular channel 119 also serves to absorb heat conducted away from motor 260 via the heat sink formed from the engagement of inner housing 116 and drive casing 240, thus helping to cool motor 260 during use. In addition, as also noted above, seal ring 270 is maintained decoupled from drive rotor 250 during use, reducing friction and potential wear on seal ring 270 as drive rotor 150 is rotated.

Once the desired tissue is removed, tissue resecting device 10 may be deactivated and removed from the surgical site. Thereafter, end effector assembly 100 may be disengaged from handpiece assembly 200 and discarded (or sent for reprocessing), while handpiece assembly 200 is cleaned and/or sterilized for reuse. As detailed above, upon disengagement of end effector assembly 100 from handpiece assembly 200, seal 270 is returned to its at-rest position, thus inhibiting fluid ingress into handpiece assembly 200 during sterilization and/or cleaning thereof for reuse.

As an alternative to handpiece assembly 200 configured for manual grasping and manipulation during use, tissue resecting device 10 may alternatively be configured for use with a robotic surgical system wherein handle housing 210 is configured to engage a robotic arm of the robotic surgical system. The robotic surgical system may employ various robotic elements to assist the surgeon and allow remote operation (or partial remote operation). More specifically, various robotic arms, gears, cams, pulleys, electric and mechanical motors, etc. may be employed for this purpose and may be designed with the robotic surgical system to assist the surgeon during the course of an operation or treatment. The robotic surgical system may include remotely steerable systems, automatically flexible surgical systems, remotely flexible surgical systems, remotely articulating surgical systems, wireless surgical systems, modular or selectively configurable remotely operated surgical systems, etc.

The robotic surgical system may be employed with one or more consoles that are next to the operating theater or located in a remote location. In this instance, one team of surgeons or nurses may prep the patient for surgery and configure the robotic surgical system with the surgical device disclosed herein while another surgeon (or group of surgeons) remotely control the surgical device via the robotic surgical system. As can be appreciated, a highly skilled surgeon may perform multiple operations in multiple locations without leaving his/her remote console which can be both economically advantageous and a benefit to the patient or a series of patients.

The robotic arms of the robotic surgical system are typically coupled to a pair of master handles by a controller. The handles can be moved by the surgeon to produce a corresponding movement of the working ends of any type of surgical instrument (e.g., end effectors, graspers, knifes, scissors, cameras, fluid delivery devices, etc.) which may complement the use of the tissue resecting devices described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A tissue resecting device, comprising:
   a handpiece assembly including a drive rotor; and
   an end effector assembly configured to engage the handpiece assembly, the end effector assembly defining a longitudinal axis and including:
      a proximal hub housing defining a fluid channel including an input and an output, the input disposed in a radially-inward facing direction relative to the longitudinal axis;
      an inner core operably disposed within the proximal hub housing and configured to couple to the drive rotor such that rotation of the drive rotor effects rotation and reciprocation of the inner core relative to the proximal hub housing;
      a cutting member extending distally from the proximal hub housing and coupled to the inner core such that rotation and reciprocation of the inner core rotation relative to the proximal hub housing effects rotation and reciprocation of the cutting member relative to the proximal hub housing; and
      a valve disposed within the proximal hub housing, the valve transitionable, in response to the rotation and reciprocation of the inner core relative to the proximal hub housing, between an open position, permitting fluid flow from the cutting member into the input of the fluid channel, and a closed position, inhibiting fluid flow from the cutting member into the input of the fluid channel, wherein the valve is disposed in the open position during a first portion of the reciprocation motion of the inner core, and wherein the valve is disposed in the closed position during a second, different portion of the reciprocation motion of the inner core,
   wherein transitioning of the valve from the closed position to the open position establishes a surge of centrifugal force to urge fluid from the cutting member into the input of the fluid channel.

2. The tissue resecting device according to claim 1, wherein the handpiece assembly further includes a fluid conduit configured to couple to the output of the fluid channel to receive fluid therefrom.

3. The tissue resecting device according to claim 2, wherein the fluid conduit is adapted to connect to a suction source to apply suction through the fluid conduit, the fluid channel, and the cutting member when the valve is disposed in the open position.

4. The tissue resecting device according to claim 3, wherein the surge of centrifugal force is greater than a steady-state suction force applied from the suction source.

5. The tissue resecting device according to claim 1, wherein the inner core is configured to reciprocate through the proximal hub housing between a proximal position and a distal position, wherein the valve is disposed in the open position when the inner core is disposed towards the proximal position, and wherein the valve is disposed in the closed position when the inner core is disposed towards the distal position.

6. The tissue resecting device according to claim 1, wherein the end effector assembly further includes a fixed outer shaft extending distally from the proximal hub housing and disposed about the cutting member.

7. The tissue resecting device according to claim 1, wherein the valve is defined by the inner core and an inner housing of the proximal hub housing.

8. The tissue resecting device according to claim 1, wherein the handpiece assembly further includes a motor disposed within a housing thereof, the motor configured to drive rotation of the drive rotor.

9. The tissue resecting device according to claim 1, wherein the end effector assembly is configured to releasably engage the handpiece assembly.

10. The tissue resecting device according to claim 1, wherein the end effector assembly further includes an elongated outer shaft fixed relative to and extending distally from the proximal hub housing, the cutting member extending through the elongated outer shaft and configured to reciprocate and rotate relative thereto to cut tissue extending into an opening defined by the elongated outer shaft.

* * * * *